(12) United States Patent
Garrett

(10) Patent No.: US 6,185,456 B1
(45) Date of Patent: Feb. 6, 2001

(54) DEFIBRILLATOR DISARM CIRCUIT UTILIZING THERMAL FEEDBACK

(75) Inventor: Michael C. Garrett, Skokie, IL (US)

(73) Assignee: Medical Research Laboratories, Inc., Buffalo Grove, IL (US)

( * ) Notice: Under 35 U.S.C. 154(b), the term of this patent shall be extended for 0 days.

(21) Appl. No.: 09/259,085

(22) Filed: Feb. 26, 1999

(51) Int. Cl.[7] .................................................. A61N 1/39
(52) U.S. Cl. ......................................... 607/5; 607/6
(58) Field of Search ............................. 607/5, 6, 4

(56) References Cited

U.S. PATENT DOCUMENTS

| | | | |
|---|---|---|---|
| 3,659,178 | 4/1972 | Gilbert et al. | 320/1 |
| 3,821,635 | 6/1974 | Kimmel et al. | 323/102 |
| 3,886,932 | 6/1975 | Suessmilch | 128/2.1 R |
| 5,312,442 * | 5/1994 | O'Phelan | 607/5 |
| 5,470,343 | 11/1995 | Fincke et al. | 607/5 |
| 5,484,452 | 1/1996 | Persson | 607/5 |
| 5,792,188 * | 3/2000 | Starkweather et al. | 607/5 |
| 5,873,893 * | 2/1999 | Sullivan et al. | 607/5 |
| 5,959,371 * | 9/1999 | Dooley et al. | 607/5 |
| 6,041,254 * | 3/2000 | Sullivan et al. | 607/5 |

* cited by examiner

Primary Examiner—Kennedy Schaetzle
(74) Attorney, Agent, or Firm—Fitch, Even, Tabin & Flannery

(57) ABSTRACT

A discharge resistor is thermally monitored under computer supervisory control. Current flow through the resistor is duty-cycle controlled to prevent thermal damage.

11 Claims, 5 Drawing Sheets

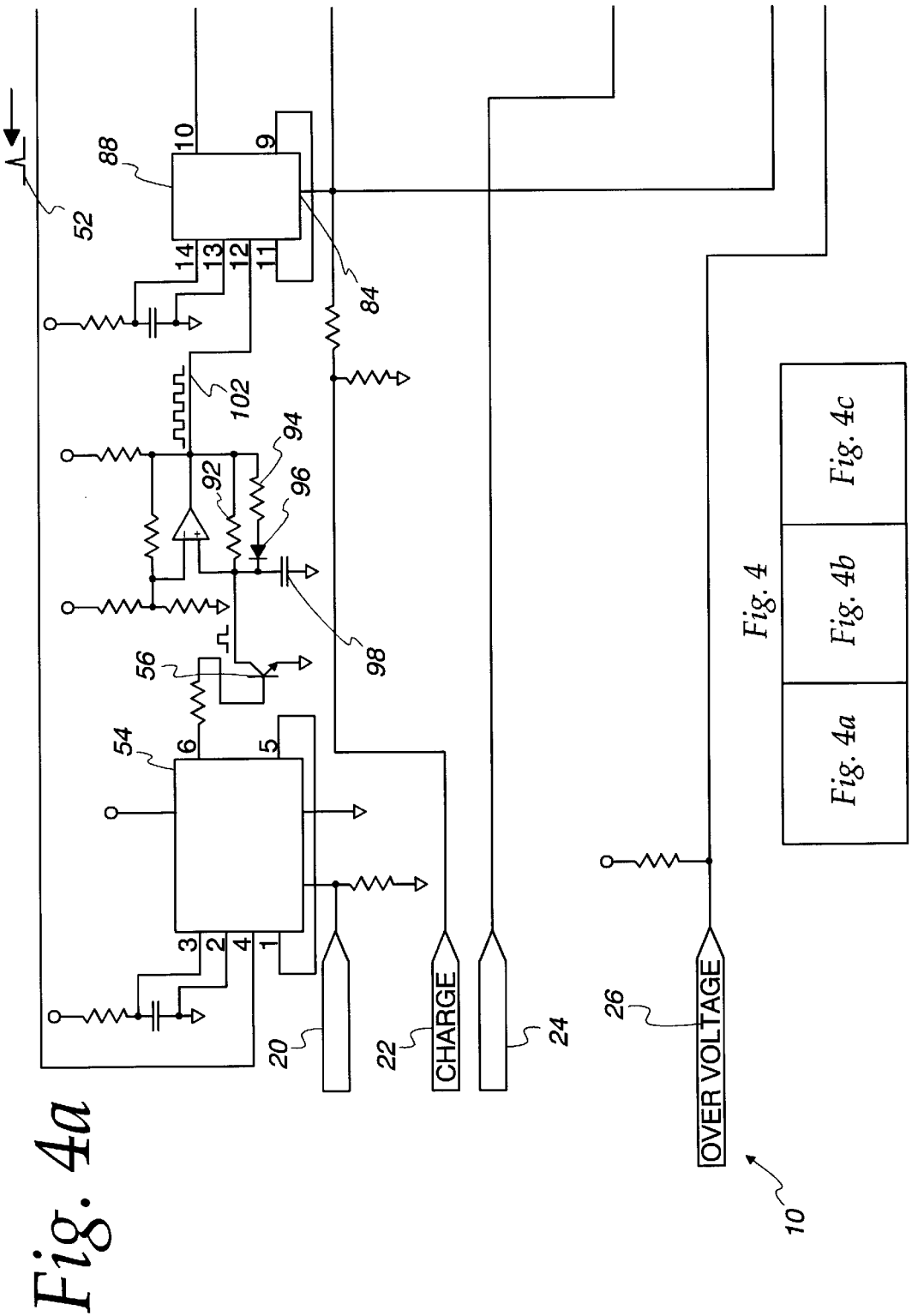

DEFIBRILLATOR DISARM CIRCUIT UTILIZING THERMAL FEEDBACK

BACKGROUND OF THE INVENTION

1. Field of the Invention

The present invention pertains to the discharging of capacitors used with defibrillators, and in particular to the automatic control of such discharge.

2. Description of the Related Art

Cardiotherapeutic defibrillators, once used only by trained medical personnel, are now being made available for use by the general population, including individuals having little or no training. The defibrillators contemplated for general use are of the automatic external type and include on-board real time diagnostic capability to intervene or otherwise control the defibrillator therapy being administered. In general, the defibrillators deliver a relatively high voltage, low energy pulse or series of pulses to a patient suffering cardiac arrhythmias, such as ventricular fibrillation. The power supply relied upon to deliver the defibrillation therapy typically comprises one or more batteries carried on board the defibrillator unit or an electrical power utility supplying mains power to a building, for example. Because of the nature of the electrical therapy required, it is not possible in a practical device to supply the therapeutic energy upon instantaneous demand, by drawing from the power source. Instead, energy from the power source must be accumulated over a certain period of time in one or more defibrillator capacitors which are later discharged to deliver the desired defibrillation therapy. It is particularly critical that the defibrillation therapy be delivered as quickly as possible, given the nature of the medical threat encountered. Accordingly, rapid charging of the defibrillator storage capacitor is required and advances in reducing charge time are still being sought.

Due to the nature of the use to which the defibrillation equipment is put, certain components employed must be carefully constructed to close performance tolerances which are expected to be closely maintained throughout the life of the component. It is important that such components are not unexpectedly stressed during unusual operating conditions, as when main power supply voltage unexpectedly drops. Also, it would be advantageous if a closer control could be exercised over the stress to which the electrical components are put.

In addition to rapid charging, practical defibrillation equipment must also be capable of rapid discharging in order to prepare for a controlled sequence of operation. Discharging may be required, for example, when a portable defibrillation unit is to be packed away for return transport to a hospital or dispatch office. At other times, discharging of defibrillator capacitor bank is required when the therapeutic action is requested to be performed at a lower capacitor voltage. For example, patients of different ages require adjustments in the defibrillation voltage applied. A patient's age may, for example, be indirectly conveyed to the defibrillation equipment by the choice of defibrillator paddles connected to the defibrillation equipment. A sophisticated, automated defibrillation unit could be informed of the paddle size and, accordingly, determine the defibrillation voltage needed, or otherwise could prompt an operator to confirm data indicating the defibrillation voltage required. In other types of defibrillation equipment in common use today, an operator is required to manually select the defibrillation voltage, either directly or indirectly through settings bearing various legends. An inexperienced or untrained field operator could, by cycling the defibrillator voltage setting, cause the voltage reduction circuit undue stress. Typically, the greatest stress is borne by a discharge resistor or the like dissipative disarmed device which can become extremely warm during this type of unusual operating condition. Unusually heavy use, even though otherwise, proper, could also cause unacceptable stress on a defibrillator disarm circuit.

SUMMARY OF THE INVENTION

It is an object of the present invention to provide a controlled defibrillator voltage reduction circuit.

Another object of the present invention is to provide a defibrillator voltage reduction circuit in which the discharge rate is automatically controlled in order to manage the stress placed on a discharge resistor or other dissipative disarm device.

These and other objects of the present invention are provided in apparatus for discharging a defibrillator capacitor, comprising:

energy consuming means for consuming energy stored in said defibrillator capacitor;

a computer means;

first monitoring means for monitoring the energy consumption of said energy consuming means and for sending an output signal in response thereto to said computer means;

control means coupled to said energy consuming means to control energy consumed thereby and to said computer means, in response to a control signal from said computer means;

said computer means including means to send said control signal to said control means to control energy consumed by said energy consuming means in response to the output signal from the first monitoring means.

BRIEF DESCRIPTION OF THE DRAWINGS

FIGS. 4a–4c together comprise a schematic diagram showing the defibrillator system in greater detail.

DETAILED DESCRIPTION OF THE PREFERRED EMBODIMENTS

Figure 1:
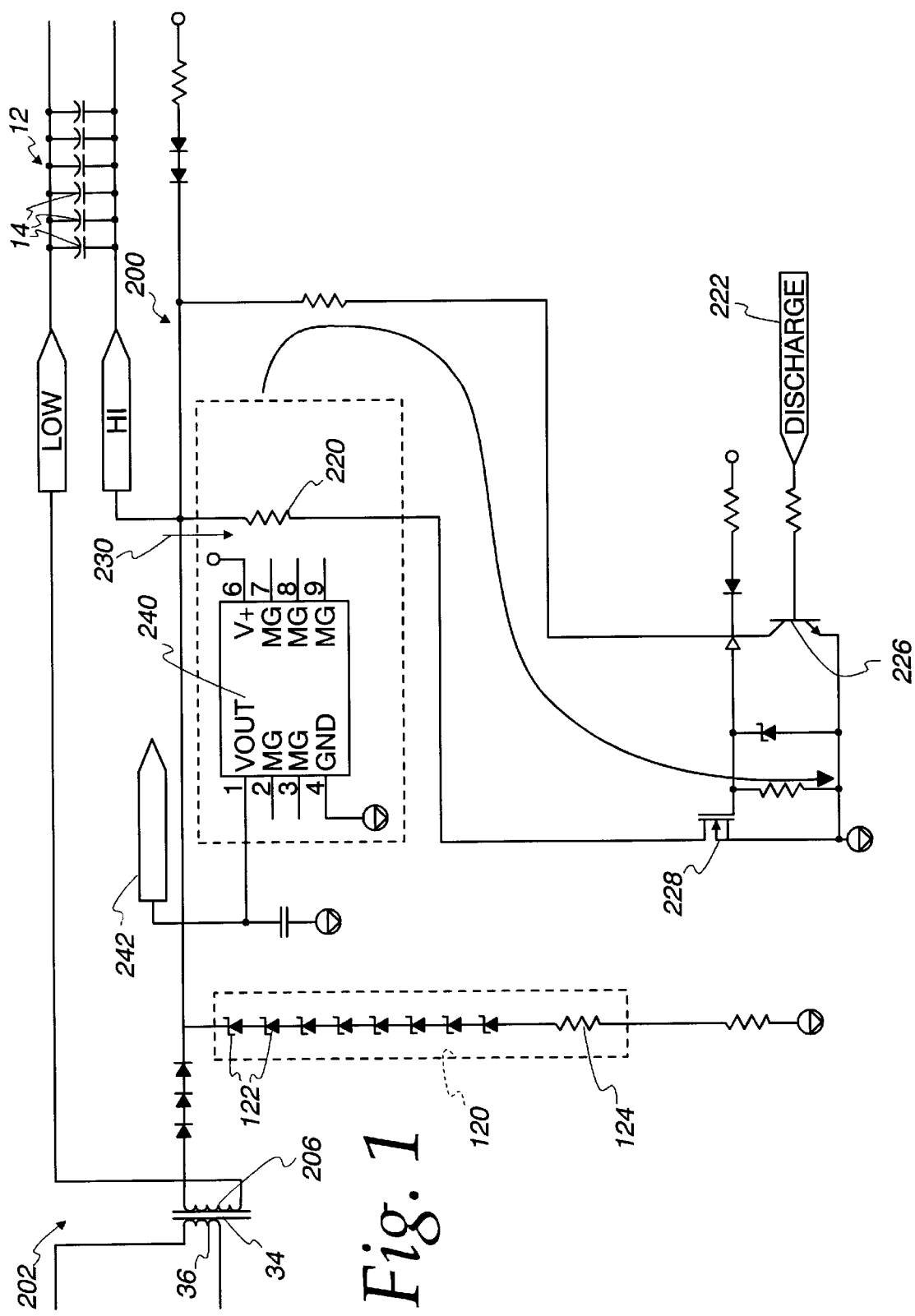
FIGS. 1a and 1b are a schematic diagram of a discharge circuit according to the principles of the present invention.
Figure 2:
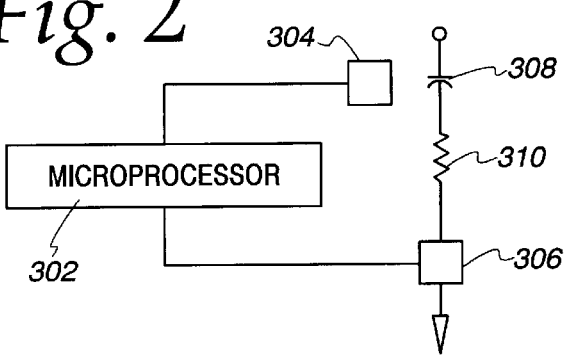
FIG. 2 is a block diagram thereof.

Referring now to FIGS. 1 and 2, a defibrillator capacitor discharge circuit is generally indicated by the reference numeral 200 in FIG. 1b. The discharge circuit 200 is shown embodied in of a defibrillator circuit portion generally indicated at 202 which includes a fly-back transformer 34 having a primary winding 36 and a secondary winding 206. A series 120 of diodes 122 and a resistor 124 control the output voltage of the transformer secondary winding. A bank 12 of defibrillator capacitors 14 are charged to an approximate value of 12 volts by an independent external charging circuit (not shown). The capacitors 14 are fully charged by operation of the fly-back transformer 34. An example of a charging circuit is given later herein with reference to FIGS. 3 and 4. It should be noted at the outset that FIGS. 1a and 1b correspond to FIGS. 4b and 4c which are repeated for convenience.

Referring to FIG. 1b, an energy consumption device, preferably in the form of a dissipative device and most preferably in the form of a discharge resistor, is indicated at 220. A DISCHARGE DISABLE signal is applied to a terminal 222 shown at the lower right corner of FIG. 1b. The terminal 222 is connected to a control device such as the microcomputer shown at the bottom of FIG. 4a. An enabling signal sent to the discharge terminal 222 turns on transistor 226 which in turn turns off power control device 228 into an open state stopping a discharge current 230 from flowing through resistor 220, thereby stopping discharging the capacitors 14 in bank 12. A conventional temperature circuit such as device member LM35 indicated by reference numeral 240 is thermally associated with discharge resistor 220. Thermal sensor device 240 outputs a signal indicative of the resistor temperature at terminal 242 which is also coupled to the microcomputer shown at the bottom of FIG. 4a.

The microcomputer 25 preferably continuously monitors the temperature of the discharge resistor 220. In response either to the resistor temperature or a calculated time-temperature value obtained each time the thermal sensor 240 is polled, the microcomputer performs a comparison with pre-set values associated with resistor 220 being at risk. The microcomputer 25 can take several different types of corrective action. For example, on over temperature conditions, the microcomputer could lift the DISCHARGE DISABLE signal at terminal 222 causing transistor 226 to open, turning on power control device 228. This action can be carried out for a pre-set "timeout", with the temperature of the resistor 220 being re-polled to determine if it is capable of further discharge operation (assuming that the microcomputer is still receiving a command for further discharge to take place). The terminal 222 is designed for DISCHARGE DISABLE as a fail safe feature upon shutdown of the defibrillator unit.

Alternatively, the microcomputer could apply a controlled frequency signal to terminal 222 to "duty cycle" the transistor 226 and in turn the power control device 228. The frequency of this signal could be either pre-set, calculated or derived from a look-up table relating the signal frequency to either the temperature or time-temperature values observed by sensor 240.

If desired, terminal 222 could be operated as a DISCHARGE ENABLE signal driving the power control device 228 into a conductive condition. As a further control strategy, the signal on discharge terminal 222 and transistor 226 could operate to selectively bias a variable resistance power control device 228 providing, at least within a specified operating range, an infinitely variable control over current flow through resistors 220.

Yet another alternative control arrangement can be implemented with microcomputer 25. Preferably, the voltage on the capacitors 14 is continuously monitored by the microcomputer. When otherwise permitted, an optimally rapid discharge of resistor 220 would be carried out under microcomputer control, as mentioned above. However, if the microcomputer determines resistor 232 to be at risk due to thermal conditions reported by sensor 240, the microcomputer could carry out a reduced discharge as a function of the capacitor voltage. Higher rates of discharge could be mandated, if desired, by the concurrence of a high voltage on the capacitor bank, a demand for defibrillation therapy at a lower energy level, and a configuration that related systems (such as the defibrillator paddles) are ready for immediate operation. If, for example, immediate operation is not cleared by the various auxiliary systems, a reduced discharge rate consistent with the thermal loading of resistor 220 and the voltage on capacitor bank 12 can be carried out while an error message is displayed to the operator and the defibrillation system "stands down" until the error (e.g., reconnection of the defibrillation paddles) is remedied.

Control strategies could also predict the thermal loading on the resistor 220 at the completion of a discharge. If, for example, there is only a slight overvoltage on the capacitor bank beyond that called for, the microcomputer program may determine that even though the resistor 220 is approaching a thermal risk condition, a full discharge rate would not result in a serious thermal overload. Such predictive control strategies could make a substantial difference because real time thermal control of the resistor 220 is subject to thermal inertia and other delays in the thermal circuit. The energy consumed by resistor 220 could also be consumed by a light bulb, motor, transducer or the like energy consuming device.

Turning now to FIG. 2, a schematic block diagram of the discharge circuit is indicated at 300. A microprocessor or other control device, such as an analog operational amplifier 302, receives temperature data from a thermal sensor 302 and, in response, sends a control signal to power control device 306 which prohibits or reduces the rate of discharge of defibrillator capacitor 308 through a dissipative discharge device 310.

Figure 4B:
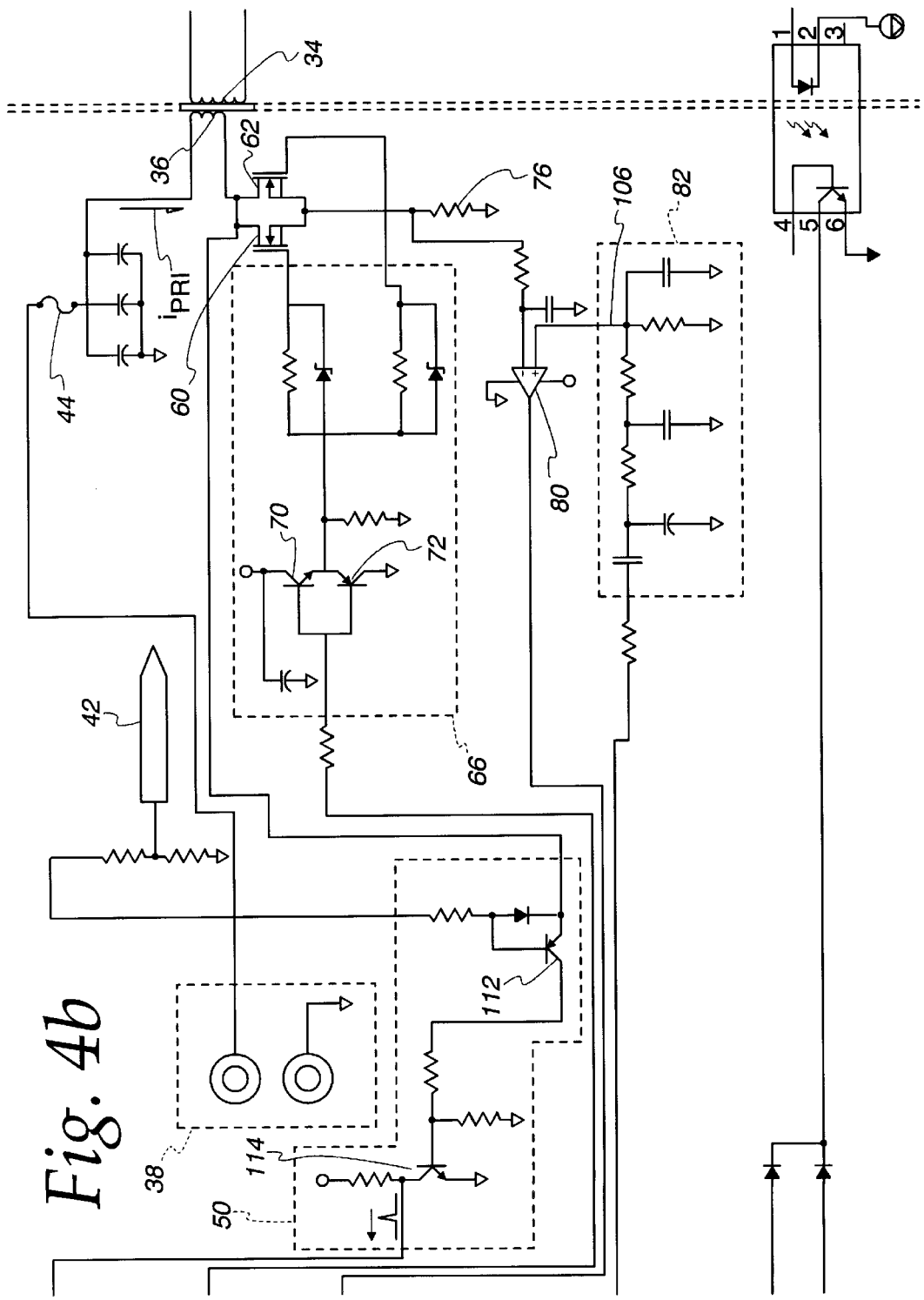
Figure 4C:
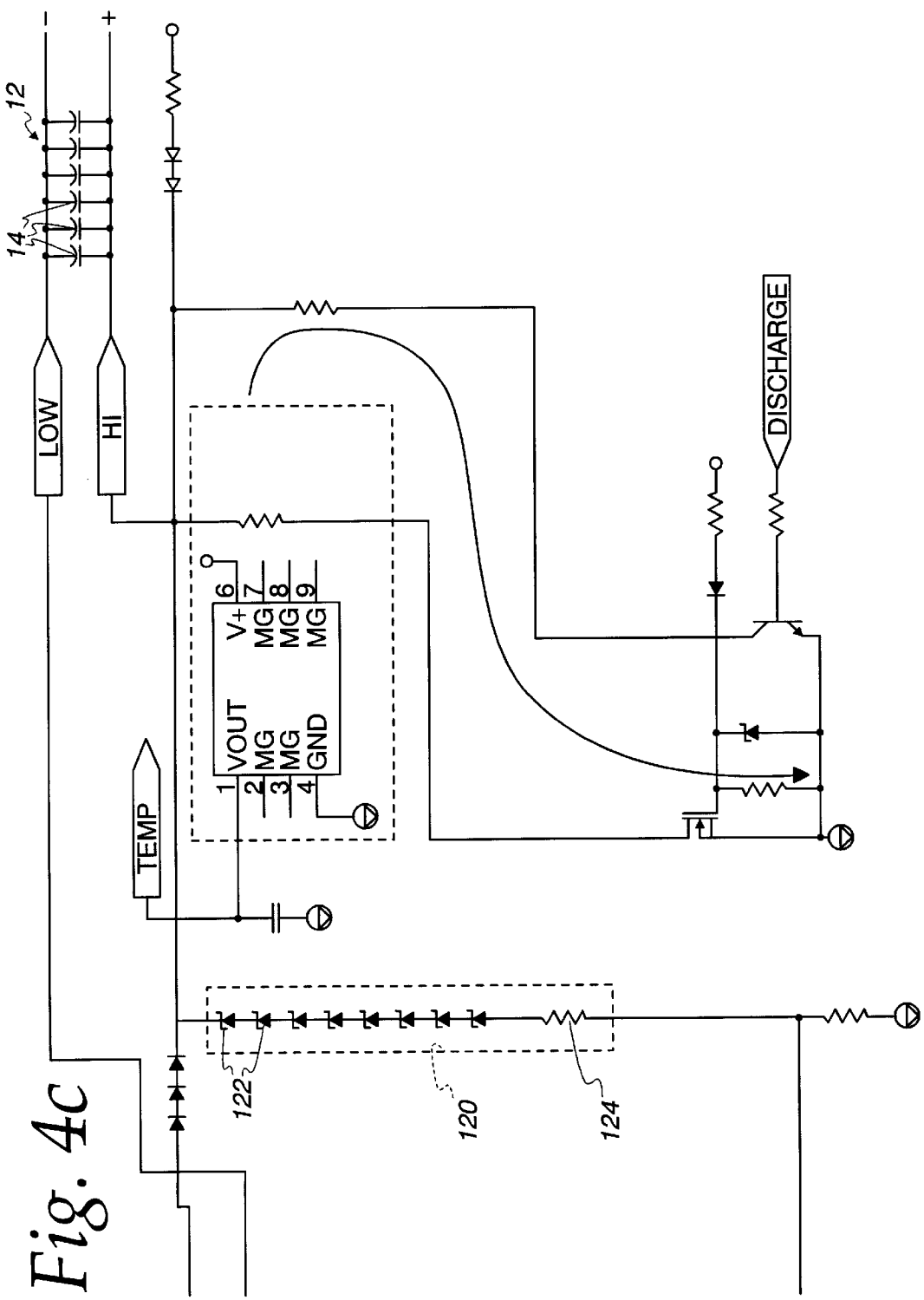

Turning now to FIG. 4, apparatus includes a circuit for charging defibrillator capacitors is generally indicated at 10. As indicated in the inset in FIG. 4, the schematic diagram is read left to right across four FIGS. 4a–4c. Briefly, the circuit operates to charge a bank 12 of defibrillator capacitors 14 shown in the upper right corner of FIG. 4c. Referring to FIG. 4a, a FAST CHARGE DISABLE TERMINAL 20 is coupled to a computer 25 or other control device which lifts a disable command signal indicating that a fast charge is required. In the preferred embodiment, program control is implemented by a digital computer, although it will become readily apparent to those skilled in the art that conventional analog circuitry or an application specific integrated circuit (ASIC) could be employed in place of the computer.

Terminal 22 is connected to the same computer 25 and receives an instruction indicating that the CHARGE DISABLE signal is to be lifted in preparation for a therapeutic event. Terminal 24 is also connected to the same computer 25 to issue a pulse signal indicating a pulse width voltage command to be described herein. Terminal 26 located at the bottom of FIG. 4a indicates to the computer 25 that an overvoltage condition has been sensed in conventional overvoltage protection device 30, shown at the bottom of FIG. 4b.

Turning to FIG. 4b, two sources of charging voltage are applied to the capacitor bank 12. One source, identified by reference numeral 125, charges the capacitor bank to an approximate twelve volt level. Power from a battery or other charger source 38 is delivered by the secondary windings of a pulse transformer 34. The primary windings 36 of the transformer 34 receive power from the energy source 38 which, for a portable external defibrillator of the preferred embodiment is delivered by a conventional 12 volt bulk input storage battery. As shown at the top of FIG. 4b, a voltage signal proportional to the battery voltage is sent to the computer 25 through a terminal 42. The voltage present at terminal 42 is also sent to computer 25. The computer 25 responds to the battery voltage at terminal 42 to regulate further charging activity if the computer, based upon recent stored data of voltage-time characteristics of the battery indicate that the battery is about to enter a cut-off condition. If desired, the computer 25 commands can be overridden so as to deliver any remaining energy in the battery, even though a battery cut-off condition is imminent. Power to the transformer primary is carried through a conventional protective fuse 44. As indicated in FIG. 4b, a current $i_{PRI}$ flows through fuse 44 and constitutes the primary current in transformer 34. As will be seen herein, the primary current is computer controlled and the function of the reference voltage developed by the circuit 82.

Referring again to FIG. 4b, a field sensor circuit 50 shown at the top of FIG. 4b senses magnetic field collapse in transformer 34 and responds by delivering a trigger pulse 52 shown in symbolic form in the upper right-hand corner of FIG. 4a. The trigger pulse is delivered to an input of a monostable pulse generator 54. A FAST CHARGE signal is also applied by the computer 25 to a second input of monostable pulse generator 54. Output from the monostable pulse generator 54 is sent to switching transistor 56, altering the operation of circuitry controlling solid state switching devices 60, 62 shown in FIG. 4b. When switching elements 60, 62 are closed, the current path through the transformer primary is completed and current $i_{PRI}$ is drawn from the bulk power supply to charge the magnetic field in transformer 34.

Referring again to FIG. 4b, driver circuitry 66, including switching transistors 70, 72, provides the driving signals to high power switching devices 60, 62 causing those devices to conduct the primary transformer current $i_{PRI}$. As the primary current ramps up, a voltage develops across current sensing resistor 76 which in turn is fed to one input of comparator 80. The energy sensing element inputted to comparator 80 could also comprise a current sensing transformer, or a Hall effect device, if desired. As will be seen herein, the other input of comparator 80 receives a computer-controllable reference voltage from circuitry 82. When the transformer current-induced voltage across resistor 76 exceeds the reference voltage supplied to comparator 80, comparator 80 sends a reset signal to a reset input 84 of a monostable pulse generator 88, shutting off switch transistors 70, 72, and in turn the solid state power control devices 60, 62, thus terminating the current flow from the power supply flowing through the transformer primary 36.

Consideration will now be given to the interaction of the three stages which control drive circuitry 66 and in turn the current flowing through the transformer primary. The third stage, comprising monostable pulse generator 88, issues a series of pulses to driver circuit 66. Each pulse has a pulse width adjusted to limit primary current "on" time in transformer 34. Monostable pulse generator 88 is triggered on the rising edges of incoming pulses and tends to produce a corresponding number of fixed width pulses. However, the output pulses from the monostable pulse generator are automatically controlled by the present invention in that the pulse width duration is cut short by a selective, voltage control RESET. The current control to the transformer is implemented by comparator 80 which operates to cut off, i.e., reset monostable pulse generator 88 as required to limit the "switch on" time allowed, thereby limiting the peak current in the transformer primary circuit.

Preferably, the monostable pulse generator 88 is of the triggerable type and responds to a pulse rate at its input which is made variable according to other aspects of the present invention. As can be seen in FIG. 4a, conductor 102 transmits a pulse train to an input of monostable pulse generator 88. Conductor 102 receives the pulse train from the output of astable multivibrator 90. The inherent frequency of the astable multivibrator current is set to a value substantially lower than that needed for an optimal charging rate. Preferably, the frequency of the a stable multivibrator 90 is chosen at a "fail safe" level (e.g., on the order of 10 kHz) to assure that, in a free-running condition (herein termed the "slow charge" rate) the fly-back transformer 34 will not become saturated in otherwise uncontrolled, reasonably anticipated operation. As a frame of reference, the "slow charge" rate requires several minutes to fully charge a capacitor bank which has been pre-charged to an approximate 12 volt level. In order to selectively obtain greater performance from the charging circuit, the pulse rate of the pulse train on conductor 102 is selectively increased to frequencies approaching 60–70 Hz according to a number of predetermined FAST CHARGE circuit controls.

Referring again to FIG. 4a, the first stage controlling operation of driver circuit 66 includes monostable pulse generator 54. As mentioned, the input of this pulse generator is triggered by trigger pulses 52 received from field collapse detector circuit 50. When a FAST RATE DISABLE signal is lifted from terminal 20, the monostable pulse generator 54 is allowed to operate, generating a pulse with each field collapse within the fly-back transformer. Thus, the triggering of pulse generator 54 is synchronized to the collapse of field within the fly-back transformer, allowing the capacitor bank to be charged as quickly as possible while avoiding saturation of the transformer core. The output of monostable pulse generator 54 is coupled through a buffer stage, including transistor 56, to a reset input of the astable multivibrator 90. This causes the astable multivibrator reset to its output pulse train, in effect introducing an "augmentation" or forced pulse to occur ahead of the next regular (i.e., circuit-determined) pulse. This in turn causes the third stage, monostable pulse generator 88, to trigger at a time earlier than it would have been triggered by a free-running second stage (i.e., operation of multivibrator 90 in a free-running mode).

The enhanced, forced triggering of monostable pulse generator 88 is, as mentioned, needed in order to attain maximum charge rate for the capacitor bank. As mentioned, without the forced triggering of monostable pulse generator 88 (with resulting added augmentation pulses) a full charge on the capacitor bank will require at least several minutes of circuit operating time. With the forced triggering afforded by the first stage (that including monostable pulse generator 54), the same full charge condition is determined in approximately five seconds. As will be appreciated, there is an unlimited number of charge rates available between a forced maximum charge rate and a lower free-running charge rate.

Consideration will now be given to the operation of comparator 80 and its associated circuitry, including voltage reference circuit 82 and primary current detection circuit comprising resistor 76. The reference voltage developed by circuitry 82, which responds to signals from terminal 24, connected to the computer 25. The computer input signals preferably comprise a fixed frequency, variable pulse width pulse train. The output of circuitry 82 is coupled to one input of comparator 80, via conductor 106. The output voltage is proportional to the width of pulses inputted to the circuitry 82. The computer 25 adjusts the width of pulses in a constant frequency pulse train, causing the reference voltage on conductor 106 to vary accordingly. The width of computer pulses present on terminal 24, the voltage at which the power switching elements 60, 62 are shut off can be directly controlled by the computer, and the voltage control can be implemented with a small number of relatively inexpensive components. When comparator 80 responds by generating an output signal, the monostable pulse generator 88 is shut off, shutting off the drive transistors 70, 72 which in turn opens the power control element 60, 62 thus interrupting flow of primary transformer current from the bulk supply 38. The present invention provides control of the peak and average power demands on the bulk power supply with relatively simple circuitry 82. If desired, circuitry 82 can be replaced with a monolithic digital to analog converter or, if desired, a simple voltage source can be used in place of the circuitry 82.

Referring again to sensing circuitry 50 which detects magnetic field collapse in transformer 34, transistors 112, 114 form a voltage sensor which senses the voltage across the primary 36 of transformer 34. A pulse is outputted from the collector of transistor 114 when the voltage across the transformer primary 36 drops back to or below the supply voltage of bulk supply 38. This pulse 52 synchronizes the three pulse defining stages which activate the driver stage. More significantly, the pulse 52 serves as a timing pulse inputted to monostable pulse generator 54 causing a retrigger of the astable multivibrator 90, producing a pulse through monostable pulse generator 88 to turn on driver stage transistors 70, 72 and hence power control elements 60, 62, starting another charging cycle.

Referring to FIG. 4c, circuitry 120 includes zener diodes 122 and a resistor 124 which provides an overvoltage control triggering sensor 30 to inform computer 25, and send a shut down signal to port 84. Circuitry 120 allows the secondary current in the transformer 34 to decay at a practical, manageable rate when the primary current is cut off, thus permitting only a relatively small direct current in the primary winding 36 when a capacitor charging is initiated.

As mentioned, the primary current through winding 36 of transformer 34 flows through resistor 76, thus setting one voltage input of comparator 80 proportional to the energy stored in the fly-back transformer. The other input of comparator 80 is set by circuitry 82 under direct control from the computer 25. As a result, the primary current in transformer 34 is compared to a reference value that, when reached, terminates the switch drive pulse flowing through control elements 60, 62. This control operation wastes very little power when the current is being reduced due to a falling bulk supply voltage. If desired, the energy signal to the comparator can from the sensor of the magnetic field of the transformer (e.g., by use of a Hall effect sensor) or from a sensor of fields about a primary current conductor (e.g., by use of a current transformer).

As will now be appreciated, the capacitor charging circuit provides two closed loops for current control. An inside loop, including comparator 80, regulates current through the transformer primary in accordance with the pulse train outlet to terminal 24 by the computer 25. The outside loop feeds back battery voltage to terminal 42 of computer 25 preventing battery cut-off by regulating the average current flow out of the battery as a function of battery voltage. The computer 25 constantly monitors battery voltage and battery current drain and when battery cut-off conditions are predicted, program control within the computer 25 adjusts the pulse train at terminal 24, forcing the comparator 80 and associated circuitry downstream of comparator 80 to reduce current flowing through control elements 60, 62, thereby reducing the average current flow through the primary winding of the fly-back transformer. As an interim control step, it is preferred that the computer attempt to provide maximum current flow to the transformer primary while sensing the battery voltage for a battery cut-off precursor condition. If the battery voltage drops to an unacceptable precursor level determined by a pre-set operating point, the computer will reduce the number of pulses in the pulse train entering terminal 24, or will transfer control to the free-running low frequency SLOW CHARGE mode of operation. As can be seen from the above, two modes of operation, one "fast charge" and the other "slow charge" are readily implemented with a minimum number of inexpensive components. Regardless of the mode of operation, the control circuit according to principles of the present invention provides an improved current mode control of both the peak and the average currents through the fly-back transformer primary, in turn controlling the saturation of the transformer core.

Figure 3:
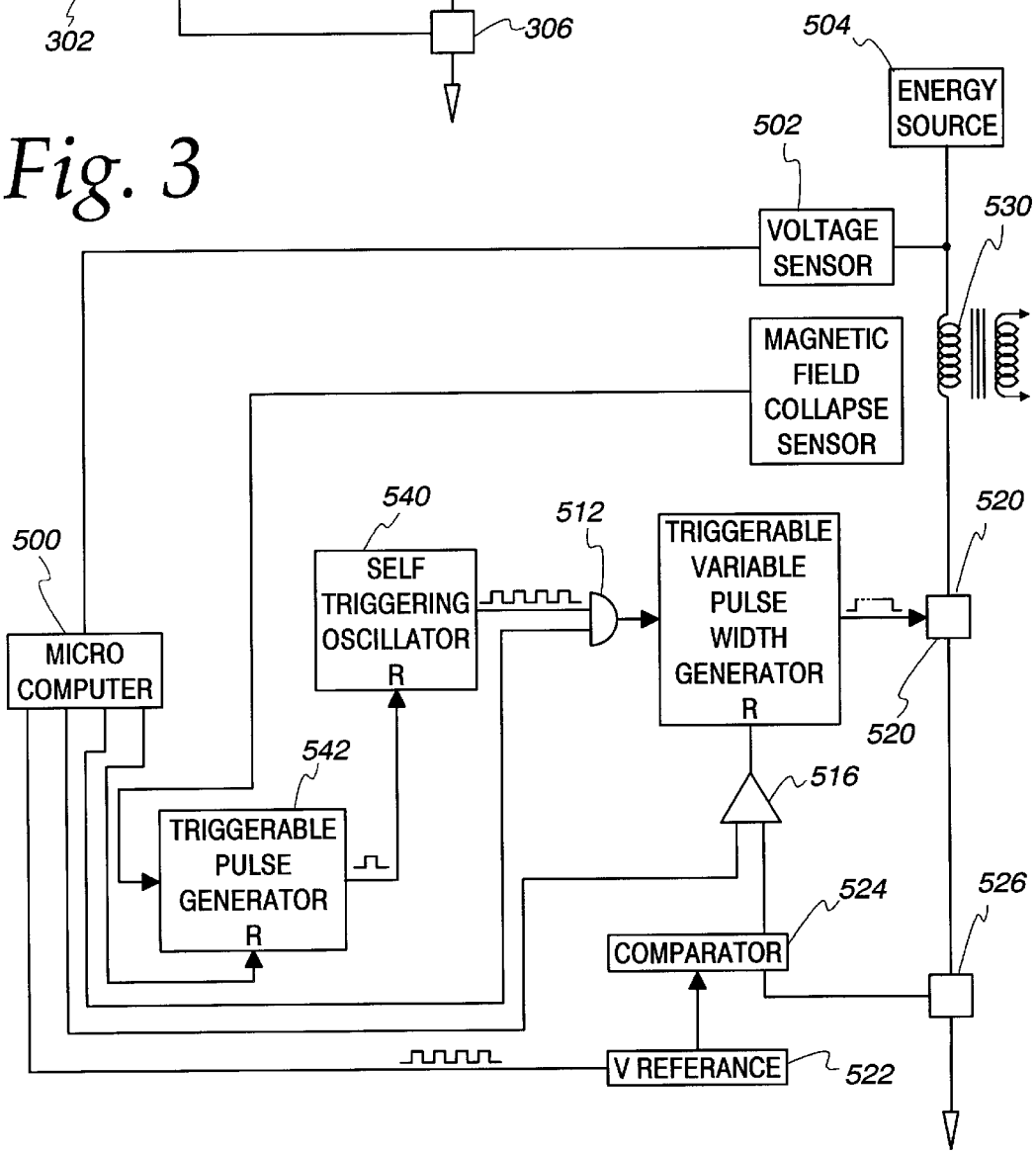
FIG. 3 is a block diagram of a defibrillator system incorporating the defibrillator discharge circuitry of the present invention.

Turning now to FIG. 3, a simplified block diagram of the circuit of FIG. 4 is shown. A microcomputer 500, analog operational amplifier or other control device receives data from voltage sensor 502, monitoring conditions of a battery or other energy source 504 for possible cut-off. The microcomputer controls input to a third stage 510, a variable pulse width generator, preferably one which is triggered by a pulse train. The third stage 510 switches transformer energy switch 520, controlling energy consumption of source 504. The microcomputer switches the incoming pulse train on and off by circuit function represented by an AND gate 512. This control lifts the energy demand on source 504. As an alternative control, the microcomputer can directly control operation of the third stage 510 by setting the third stage by circuit function represented by an OR gate 516. The microcomputer could, for example, send continuous RESET commands to the third stage 510, or could "flash" the third stage at spaced apart intervals. The microcomputer has further control over the third stage by applying an input to reference stage 522, altering the reference level outputted by the stage 522. The inputs are preferably in the form of pulses, but could be a voltage ramp, frequency or current, for example. Stage 522 preferably operates on a voltage basis, but could operate on a current, frequency or other basis as well. The reference level is applied to a comparator 524 which receives a second input from an energy sensor 526 associated with the current, voltage, electric or magnetic fields of the energy source 504 and/or the fly-back transformer 530.

A synchronizing trigger pulse is generated by; the cycling of the fly-back transformer, and preferably by the collapse of its magnetic field. The synchronizing trigger pulse may; be applied directly to the RESET point of a second stage 540, but preferably is buffered through a first stage 542 to provide a desired pulse definition in a stage made switchable under control of the microcomputer 500. The first stage is preferably a triggerable pulse generator, such as a monostable pulse generator. Most preferably, the first stage output is in pulse form, but could be in voltage, circuit or frequency form, if desired. The second stage 540 comprises a reference timing source, such as a clock chip, but preferably comprises a self-triggering oscillator and most preferably comprises an astable multivibrator whose output is fed to AND gate 512. The second stage preferably operates in a pulse mode, but could operate in a current, voltage or frequency mode as well to provide a resettable clocking control of the third stage 510. The third stage 510 has an output (preferably a pulse output) duration controllable by comparator stage 524 to provide duty cycle control of the switching stage 520. The pulse duration of stage 88 in the absence of a current reset pulse can be controlled by the maximum time out of the monostable multivibrator 510 to provide a maximum peak current or fail safe so the unit will continue in the absence of a reset pulse from 524.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. Apparatus for discharging a defibrillator capacitor, comprising:

energy consuming means for consuming energy stored in said defibrillator capacitor;

a computer means;

first monitoring means for monitoring the energy consumption of said energy consuming means and for sending an output signal in response thereto to said computer means;

control means coupled to said energy consuming means to control energy consumed thereby and to said computer means, in response to a control signal from said computer means;

said computer means including means to send said control signal to said control means to control energy consumed by said energy consuming means in response to the output signal from the first monitoring means.

2. The apparatus of claim 1 wherein said energy consuming means comprises a dissipative device, at least partly converting the stored energy to heat.

3. The apparatus of claim 1 wherein said energy consuming means comprises an electrical resistor.

4. The apparatus of claim 1 wherein said control means controls current flow through said energy consuming means.

5. The apparatus of claim 1 further comprising a second monitoring means coupled to said computer means, for monitoring energy in said defibrillator capacitor, said computer means sending said control signal to said control means to stop further consumption of energy in said energy consuming means when a predetermined target energy level of said capacitor is reached.

6. The apparatus of claim 1 wherein said computer means sends said control signal to said control means to lessen energy consumed by said energy consuming means when the energy consumption level of said energy consuming means rises above a predetermined critical level.

7. The apparatus of claim 3 wherein said first monitoring means monitors the temperature of said electrical resistor.

8. The apparatus of claim 1 wherein said control means, in response to said control signal, terminates power consumption in said energy consuming means.

9. The apparatus of claim 1 wherein said control means, in response to said control signal, reduces power consumption in said energy consuming means.

10. The apparatus of claim 1 wherein said control means, in response to said control signal, temporarily delays subsequent power consumption in said energy consuming means.

11. The apparatus of claim 1 wherein said control means comprises a solid state current control device.

* * * * *